United States Patent [19]

Ylander et al.

[11] Patent Number: 5,115,813
[45] Date of Patent: May 26, 1992

[54] ULTRASOUND METHOD AND APPARATUS FOR EXAMINING DENSE TISSUES, IN PARTICULARLY DENTAL TISSUE

[75] Inventors: Kimmo Ylander, Forssa; Pentti Mattila, Tampere, both of Finland

[73] Assignees: Hollming Oy, Rauma; Parma Oy, Forssa, both of Finland

[21] Appl. No.: 469,441
[22] PCT Filed: Oct. 14, 1988
[86] PCT No.: PCT/FI88/00170
 § 371 Date: Apr. 12, 1990
 § 102(e) Date: Apr. 12, 1990
[87] PCT Pub. No.: WO89/03195
 PCT Pub. Date: Apr. 20, 1989

[30] Foreign Application Priority Data

Oct. 14, 1987 [FI] Finland ................................ 874523

[51] Int. Cl.⁵ .................................................. A61B 8/00
[52] U.S. Cl. ............................. 128/660.01; 128/660.07
[58] Field of Search ..................... 128/660.01, 660.06, 128/660.07, 774; 73/625, 626, 602

[56] References Cited

U.S. PATENT DOCUMENTS 4,610,255 9/1986 Shimura et al. .............. 128/660.07

Primary Examiner—Francis Jaworski
Attorney, Agent, or Firm—Birch, Stewart, Kolasch & Birch

[57] ABSTRACT

The invention concerns an ultrasound based measurement method and an apparatus for examining dense tissues in particular. According to the method, the measured object (17) is subjected to a high-frequency ultrasound signal, and echoes returning from the object (17) are converted into electric signals. According to the invention, either the object (17) or the ultrasound transducer (36) is vibrated at a low-frequency and the level of the low-frequency vibrating signal is detected from the echo signal, whereby interface locations of the vibrating object (17) can be determined from the maximum values of the detected low-frequency signal in relation to the transmitted high-frequency pulse.

11 Claims, 6 Drawing Sheets

ULTRASOUND METHOD AND APPARATUS FOR EXAMINING DENSE TISSUES, IN PARTICULARLY DENTAL TISSUE

BACKGROUND OF THE INVENTION

The present invention relates to a measurement method for examining dense tissue with the help of ultrasound.

The invention also relates to a measurement apparatus for the implementation of the method.

In conventional methods, the examination of dense tissue is performed using X-ray machines. Also apparatuses for measuring dense tissue by means of ultrasound are known in the art. The publication JOURNAL OF CLINICAL ULTRASOUND (No. 13, October 1985, pages 597...600, article "Development and Application of an Ultrasonic Imaging System for Dental Diagnosis"), describes an ultrasound measurement method for examining teeth.

Because of the health hazards involved with X-rays, it is impossible to obtain real-time information about the treatment operation; instead, one must be satisfied with single pictures. Conventionally, the preparation of exposing and developing an X-ray picture takes a relatively long time, about 7...10 minutes. The ultrasound equipment currently used in medicine applications further require a computer which must be able to perform relatively complicated computations, and even with a powerful computer it is, e.g., impossible to reliably define the form of the root channel of a tooth or the position of a broach needle in the channel.

SUMMARY

The aim of the present invention is to overcome the drawbacks of the aforementioned prior art technology and to provide a completely novel ultrasound-based measurement method and apparatus for examining dense tissue.

The invention is based on subjecting the dense tissue under examination to low-frequency vibration. A high-frequency ultrasound transmitted to the tissue is modulated by the low-frequency vibration. The reflected ultrasound signal is processed by timed gating, and the vibration signal component is band pass filtered for further processing. Interfaces of the dense tissue are revealed by the amplitude maxima of the processed signal.

Consequently, the method in accordance with the invention provides for a real-time localization of tissue interface profiles as well as treatment instruments during the treatment operation. The apparatus is easy to use and is harmless to the patient. Furthermore, the apparatus is cost-effective in terms of attained resolution and ease of use.

BRIEF DESCRIPTION OF THE DRAWINGS

In the following, detailed description the invention will be set forth in more detail by means of the exemplifying embodiments in accordance with the attached drawings, wherein.

DETAILED DESCRIPTION OF THE INVENTION

Figure 1:
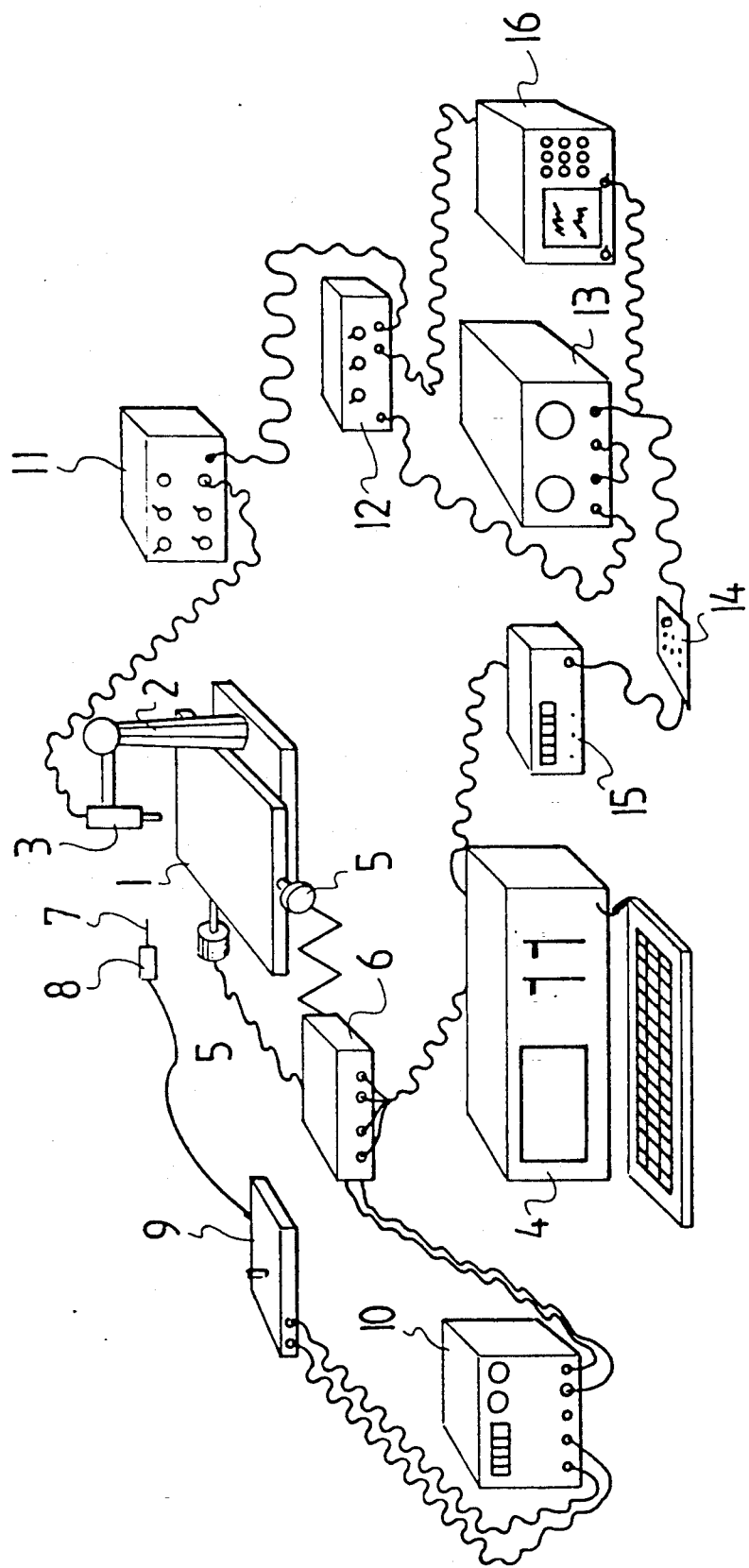
FIG. 1 shows a measurement system in accordance with the invention.

Using a laboratory setup illustrated in FIG. 1, a tooth under examination was scanned by means of an X-Y table 1 under a transducer 3 mounted to a drill arm 2. The X-Y table was controlled by a computer 4 via stepper motors 5 attached to the table's micrometer screws. In addition, between the stepper motors 5 and the computer 4, there was attached a separate controller 6, which served as a buffer amplifier for the stepper motors 5. The transducer 3 was a focused 5 MHz ultrasound transducer. Normally, the ultrasound transducer 3 comprises both a transmitter and a receiver section. Currently, most transducers are made of a ceramic piezoelectric material. A needle probe 7 was attached to the metal foil of a miniature buzzer 8 with the help of contact cement. The miniature buzzer 8 was driven by an oscillator 9, which had an oscillating frequency adjustable in the range of 200...600 Hz. The input power of the oscillator 9 was about 4 W, however, the produced output intensity level remained appreciably lower than in commercially available vibrators. A conventional laboratory power supply was used as a power supply 10. Required energy pulses to the transducer were generated by a pulser 11, which also served as a receiver and amplifier for the received echo signals. The received echo pulse was gated by a gating unit 12 with such a timing as to allow only the echo from the area under examination to pass through the gate. A filter 13 was used for extraction of the vibration frequency of the needle 7 by band pass filtering from the echo pulse, and a rectifier 14 provided the vibration level signal by rectification. The detected signal level was measured by a voltage meter 15, integrated to the system and controlled by the computer 4. The waveforms were monitored by an oscilloscope 16. In addition, the computer 4 supervised the entire measurement session and collected measurement data onto a diskette. The sweep pattern over the tooth under examination was organized in a 25 by 40 cell matrix, in which the cell size was $0.5 \times 0.5$ mm$^2$. The recorded voltage levels were stored on diskettes. Each measurement session over one examination area took about 45 minutes. The examined object was a swine jawbone.

The measurements were performed using the following basic settings: The distance of the transducer 3 from the needle probe 7 was approx. 20 mm, the transducer drive signal frequency was 5 MHz, the delay of the needle echo in water was approx. 25 us, and the needle vibrating frequency was approx. 500 Hz.

The tooth under examination was immersed in water, and the rear teeth (molars) were selected for examination. The bath temperature was approx. 20° C. Data stored on a diskette was analyzed using a BASIC-language program. Input data for the program was taken from the high levels of signal voltage values caused by the needle vibration as well as the voltage levels caused by the tooth's vibration where detectable from the noise floor. Picture generation onto the screen took about one minute. The slowness of program execution was mainly related to the programming language used. Successful results in examinations were obviously also attained by wetting the tooth under examination and placing a rubber bladder between the tooth and the transducer.

Figure 2:
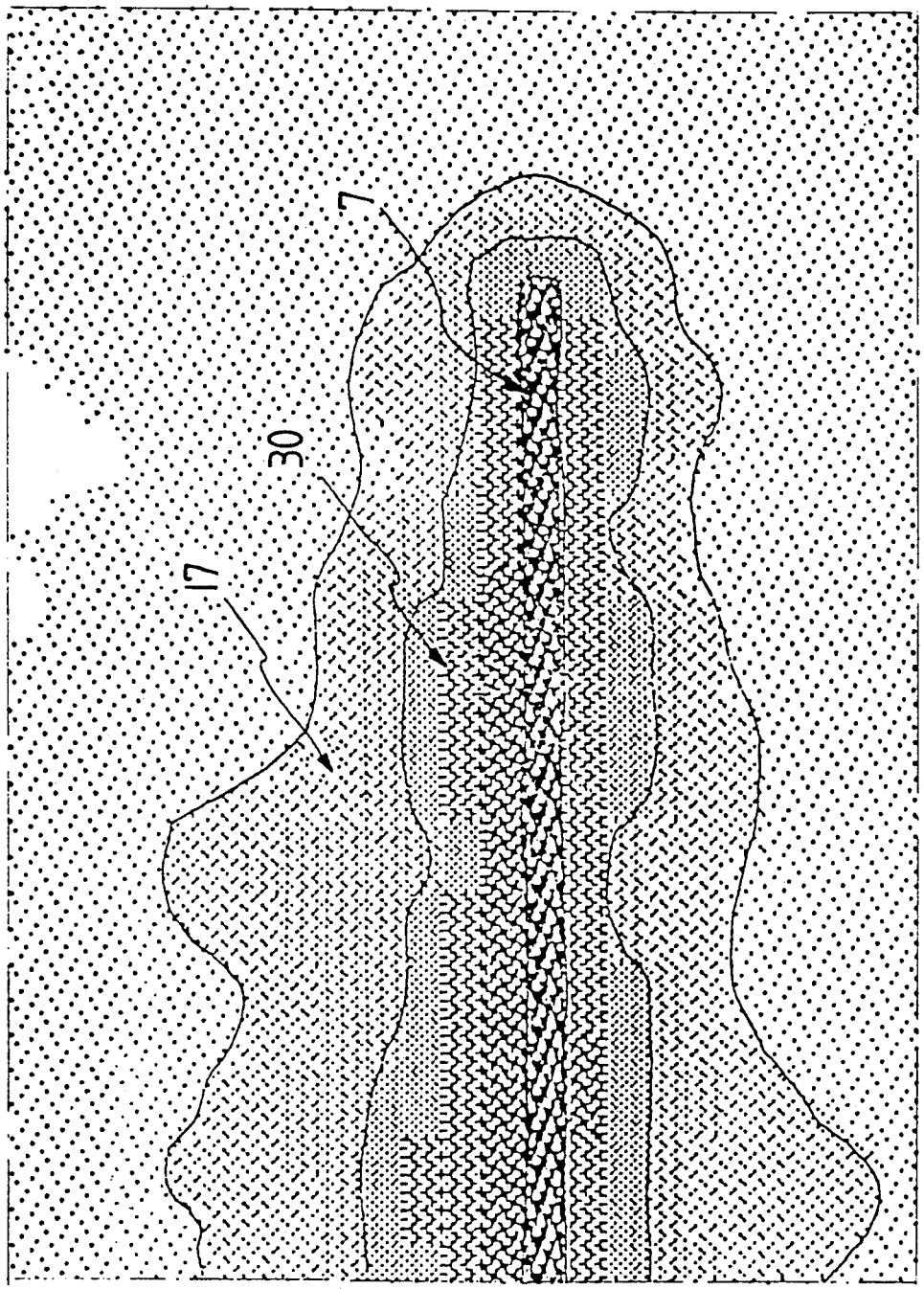
FIG. 2 shows a computer-processed image obtained by means of the system in accordance with the invention.

Illustrated in FIG. 2 is the measured matrix in approx. 12-fold enlargement. Thus, the matrix cell in the figure has dimensions of approx. $6 \times 6$ mm$^2$. The matrix represents one longitudinally sectioned slice of the tooth. Each matrix cell corresponds to one measurement result, which in practice is related to one measured DC voltage value. The needle probe 7 is visible in the middle of the figure as a horizontal bar-like area with the darkest rasterization. The jawbone is to be found at the right side of the figure. Thus, the location of the needle probe is easily definable with the help of the arrangement in accordance with the invention. Further, the identification of the tooth profile against the background is possible by averaging several subsequently taken pictures. The illustration is enhanced with border lines that define the pulp cavity 30 and the outer surface of the tooth 17.

The quality of measurement results was not essentially influenced by the operating frequency of the modulating needle. By contrast, the needle operating frequency had a significant effect on the measurement speed. A higher frequency resulted in a correspondingly faster measurement. Additionally, the disturbance level was related to the needle operating frequency. Namely, problems arose from the difficulty of finding such a vibrating frequency, at which the interaction of the pulser's pulse rate (approx. 5.5 kHz) with the power line (50 Hz) disturbances would be at a minimum. A proper frequency range was found at 200...800 Hz. In commercial applications the pulse rate should be increased to about 20 kHz so that the needle vibrating frequency could be about 1 kHz. In this manner, the measurement speed would be sufficiently fast, and furthermore, filtering of the useful signal would be easy to realize.

Figure 3:
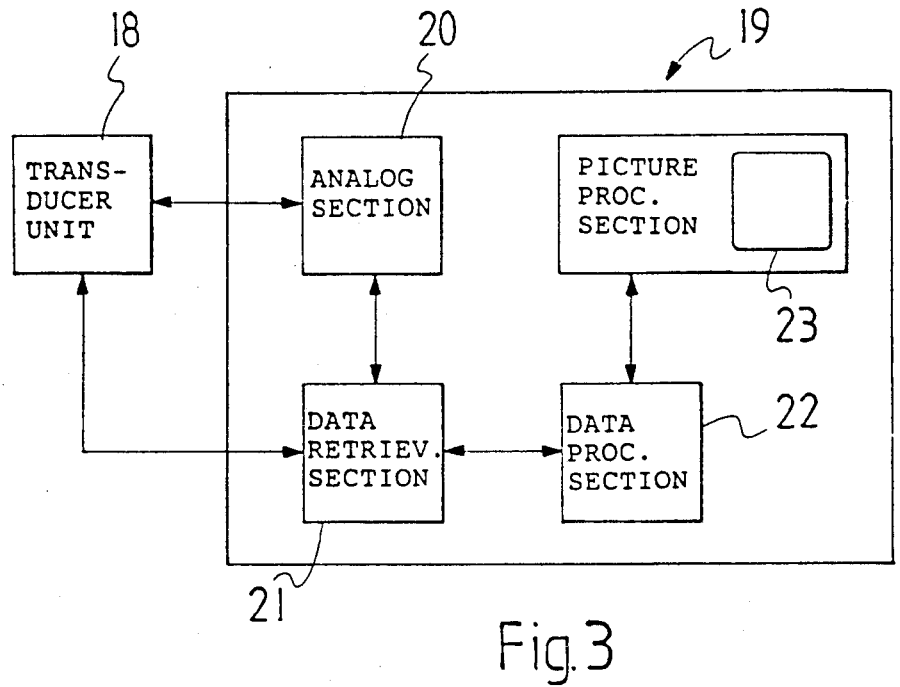
FIG. 3 shows in a block diagram the measurement system in accordance with the invention.

According to FIG. 3, a commercially produced measurement apparatus comprises a transducer unit 18 and an analyzer unit 19, which further comprises an analog section 20, a data retrieval section 21, a data processing section 22, and a picture processing section 23. In addition, the system includes a vibrator (not shown), which is a compressed-air operated pulp treatment device conventionally used by dentists. The transducer unit 18 includes a linear array ultrasound transducer as well as an actuator mechanism for moving the transducer. This arrangement replaces the X-Y table used in the system during laboratory experiments. The transducer unit 18 also includes the electronic circuits required for amplification of transducer signals and control of the actuator mechanism. The design of the transducer unit 18 resembles an electric toothbrush, which is pushed against the tooth during the examination. The transducer unit 18 is cabled to the analyzer unit 19. The purpose of the data retrieval section 21 is to control the measurement and to gather measurement results from the analog section 20 to the RAM memory. The data processing section 22 fetches measurement results from the memory of the data retrieval section 21 and performs required operations for pattern recognition. The picture processing section 23 generates the image files and controls the CRT or other similar output device. The system is capable of achieving a picture generation and update rate of at least 1 picture/10 s.

Figure 4:
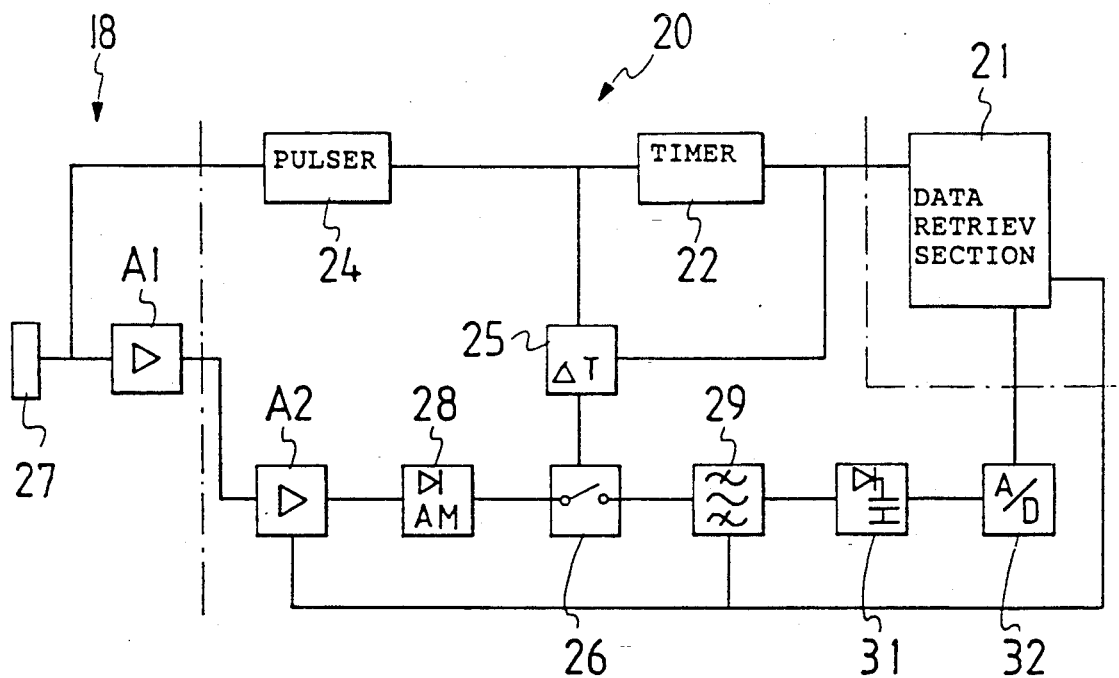
FIG. 4 shows in a block diagram one measurement channel in the system illustrated in FIG. 3.

Illustrated in FIG. 4 is one measurement channel of the analyzer unit 19 serving one transducer. The total number of channels equals the number of transducers in the linear array. The data retrieval section 21 controls the operation of the actual transducer unit 18 and the analog section 20. The data retrieval section 21 gives required control information to the timer 22 and controls the gain of the preamplifier $A_2$ as well as the length of windowing delays. The timer 22 delivers control pulses $U_0$ to pulser 24 and issues the start moment of the windowing delay to a delay section 25. The programmable delay section 25 generates a required control signal $U_8$ of the gating window to an analog switch 26. The pulser 24 delivers control pulses $U_1$ to the transducer 27 at a level matched for the ultrasound transducer. The ultrasound transducer 27 is of the pulse echo type. The amplifier $A_1$ amplifies the echo signal $U_1$ by approx. 20 dB in order to obtain a sufficiently high signal $U_2$ to be transferred by the cable to the analyzer unit 19. Voltage level of an echo signal $U_2$ amplified by a controllable amplifier $A_2$ is adjusted to a proper level for AM detection. An AM detector 28 generates a signal $U_4$ which is the envelope signal of an amplified echo signal $U_3$. An analog switch 26 gates for further processing an echo signal $U_5$, which is the echo received from the desired depth to be examined. A bandpass filter 29 is used to separate a modulating vibrating frequency $U_6$ from the echo signal $U_5$. An amplitude signal $U_7$ of the vibrating frequency is detected by rectification from the filtered vibration frequency signal $U_5$ by a rectifier 31. The rectified signal $U_7$ is converted by an A/D converter 32 into an appropriate format for digital processing.

Figure 5:
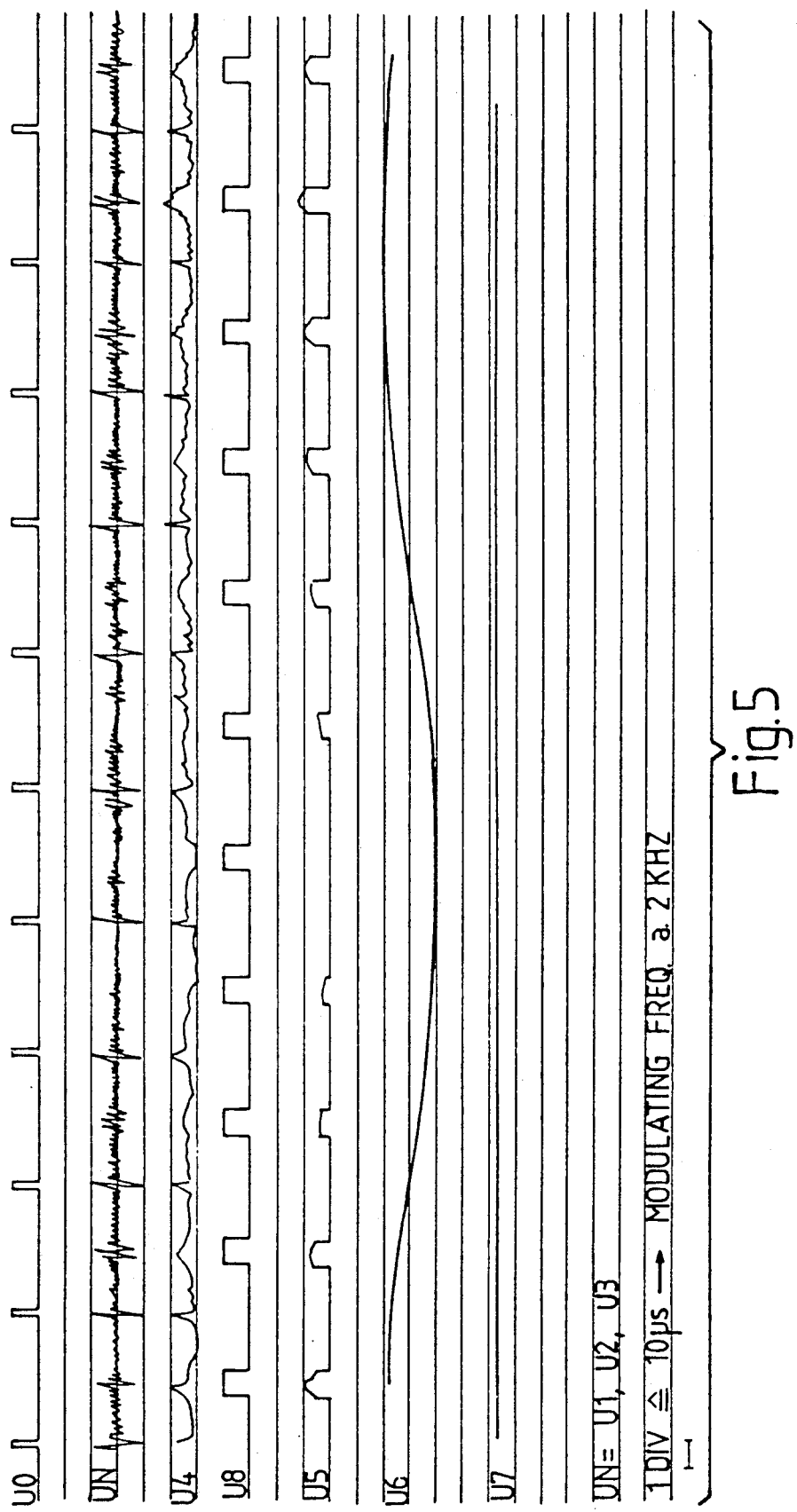
FIG. 5 shows a timing diagram of the signals over one vibrating cycle in the measurement system illustrated in FIG. 4.

Illustrated in FIG. 5 are the waveforms over one vibrating cycle at different points of the exemplifying block diagram shown FIG. 4. Prior to the illustrated cycle, a sufficiently high number of vibrating cycles are measured so that the voltage level of signal $U_7$ has already received its final value. One division of the diagram corresponds to approx. 10 us so that the modulation frequency is about 2 kHz.

Figure 6:
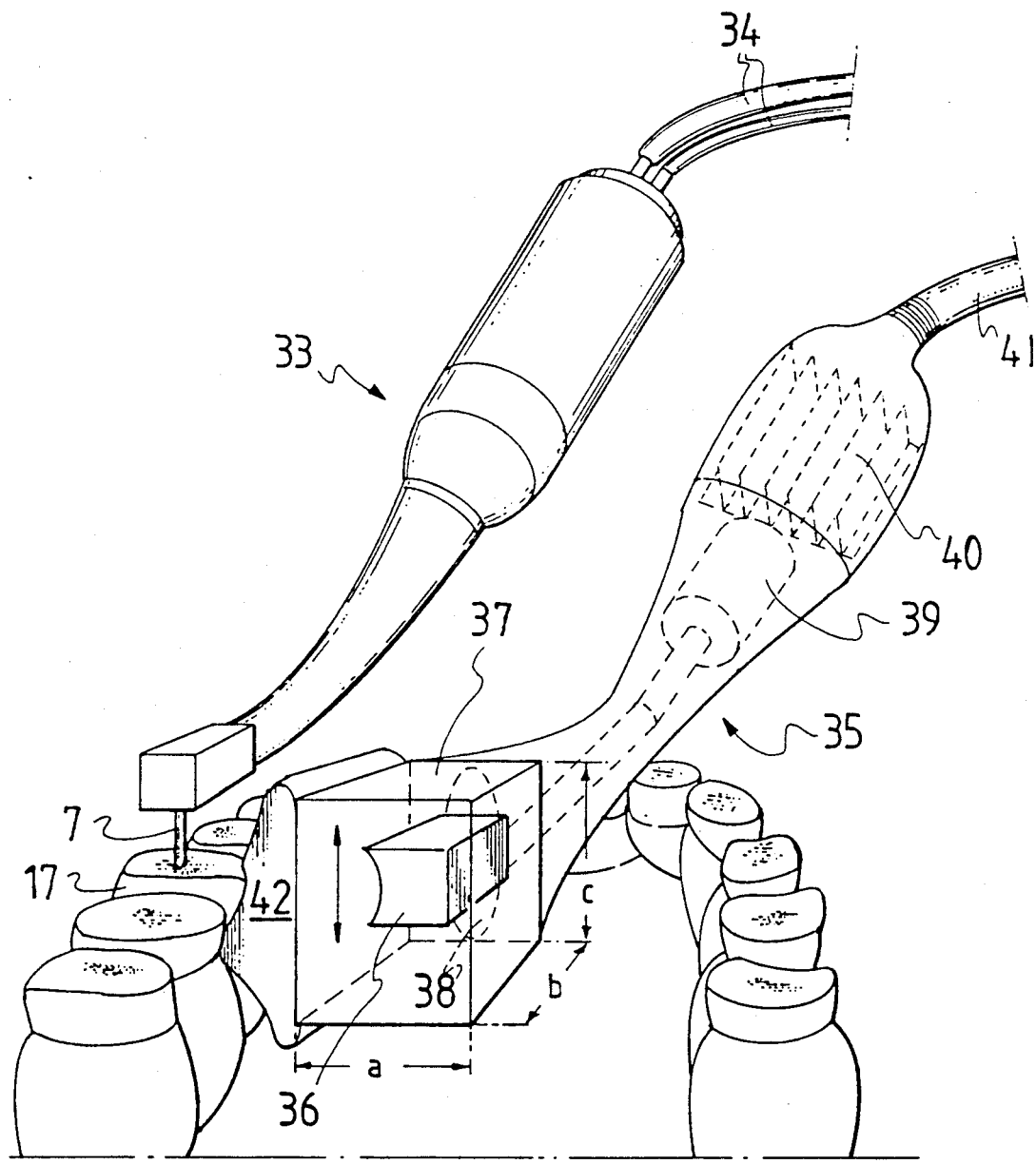
FIG. 6 shows in a perspective view another measurement system in accordance with the invention.

In accordance with FIG. 6, a needle 7 of a root channel broach 33 is inserted into the pulp of a tooth 17. The broach needle 33 is operated by compressed air, which is led to the broach instrument 33 via hoses 34. The ultrasound transducer unit 35 proper consists of a linear array transducer 36, which comprises of, e.g., 8 separate transducers. The linear array transducer 36 is mounted within an array body 37 whose dimensions are: depth a approx. 16 mm, length b approx. 20mm, and height c approx. 20 mm. The array transducer 36 is movable within the body 37 about its longitudinal axis with the help of a motor 39 mounted to supporting arm of the ultrasound transducer unit 35 and an actuator mechanism 38 mounted integral with the transducer body 37. Between the transducer body 37 and tooth 17 is inserted a bladder 42, filled with, e.g., water. Close to the actuator motor 39 in the handle part of the ultrasound unit 35 is mounted an electronics unit 40, which serves for the control of the motor 39 and reprocessing of signals. The measurement signals are routed via a cable 41 for further processing.

Figure 7:
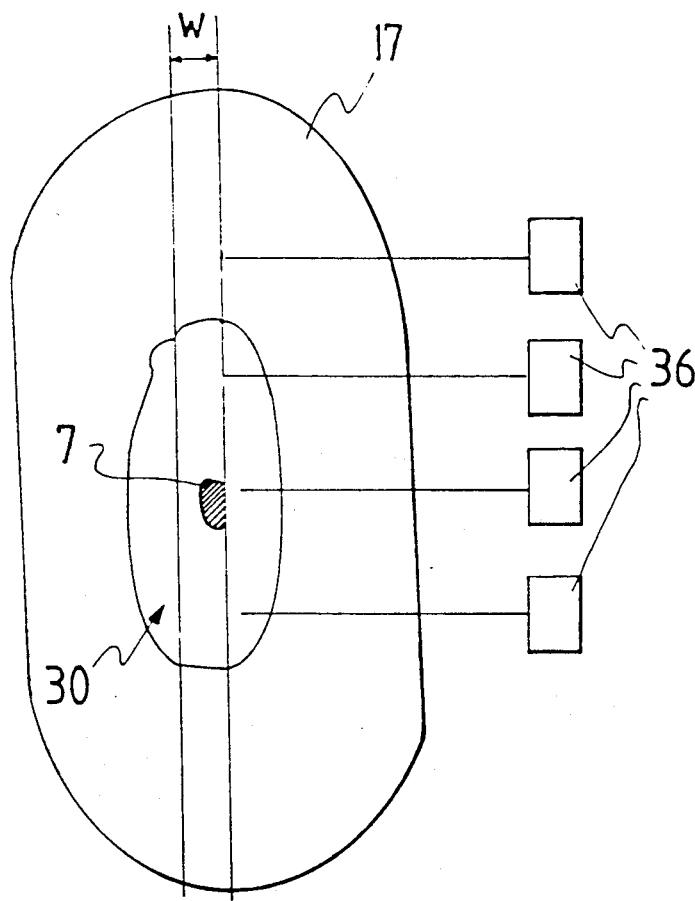
FIG. 7 shows in a partially diagrammatic top view the operation of the system illustrated in FIG. 6.

In accordance with FIG. 7 the thickness w of the detected tissue slice is determined by the size of the gating window. With a narrower window, a thinner slice is analyzed, which consequently offers an improved depth resolution by narrowing the gating window. Hence, the depth location of the slice is determined by the timed shifting of the window. Consequently, the further the gating window is shifted on the time scale from the send instant of the pulse, the deeper the slice under examination is shifted along the depth axis. By virtue of the modulation generated by the vibration of the needle 7, the echo signals obtained from the array transducer 36 that is i.e., the echoes received from the needle and other vibrated objects present a signal level significantly higher than any other signals received from other areas within the gated signal window.

The operating parameters of an apparatus according to the invention may be varied as follows: vibrator's vibrating frequency approx. 100...1000 Hz, appropriate ultrasound frequency approx. 3...15 MHz, and echo signal amplification approx. 20...60 dB.

The method in accordance with the invention can be used in addition to the medical applications, also for examining such physical composite structures, in which hard material is combined with pliabe material.

Replacing the vibration of the measured object, the transducer itself may alternatively be vibrated at a low frequency. An essential characteristic of an embodiment in accordance with the invention is the relative movement between the measured object and the transducer at a low frequency.

What is claimed is:

1. An ultrasonic method for examining an ultrasonic medium including dense tissues, said method being repetitively performed at periodic intervals, comprising the steps of:
    generating a high-frequency ultrasonic pulse by means of an ultrasound source (36),
    transmitting the ultrasonic pulse to an object (17) under examination,
    converting echo signals returning from the object (17) into electrical signals,
    determining the intensity and delay of returning echo signals in relation to the pulse transmitted to the object under examination,
    generating an image of the measured object (17) under examination from the determined delay and intensity,
    vibrating the measured object (17) or the ultrasound source (36) at a low frequency, and
    wherein the converting step further includes detecting and extracting a signal level of the low-frequency vibration signal from the echo signal in order to reveal the location of interfaces of the vibrating object(17) from the delays of the maximum values of the detected low-frequency signal relative to the transmitted high-frequency ultrasonic pulse.

2. A method in accordance with claim 1 wherein said step of vibrating comprises vibrating the measured object (17) at a frequency in the range of 100...1000 Hz.

3. A method in accordance with claim 2 wherein the object (17) under examination comprises a tooth and said step of vibrating includes inserting a compressed air operated needle (7) into a root channel (30) of the tooth.

4. A method in accordance with claim 2 wherein the step of detecting and extracting the signal level of the low-frequency vibrating signal comprises detecting the echo signal, gating the detected echo signal, filtering the gated echo signal, and rectifying the filtered signal, whereby the interface locations of the vibrating object 17 can be determined from the time relationship of the maximum value of the rectified signal to the transmitted ultrasonic pulse.

5. Ultrasonic measurement apparatus for examining an ultrasonic medium including dense tissues, comprising:
    an ultrasonic pulse generator (24), for generating a drive signal,
    an ultrasonic transducer (36) connected to the pulse generator (24), said transducer converting the drive signal into an ultrasonic pulse transmitted towards an object (17) under examination,
    an ultrasonic receiver (36) for converting an ultrasonic echo pulse reflected from said object into an electric signal, and
    a measurement and analyzer system (19) coupled to the receiver (36) for determining the intensity and delay of a vibration signal received by the receiver (36) in relation to the the ultrasonic pulse transmitted thus making it possible to generate a model of said object under examination,
    said system further comprising, a vibrator (33) for vibrating said object (17) or the ultrasound transmitter (36) with a relatively low frequency signal, and
    detection apparatus (20) coupled to said receiver (36), for detecting the level of the low-frequency vibrator signal from the echo signal for determining the interface locations of said object (17) from the maximum values of the low-frequency vibrator signal in relation to the drive signal.

6. An apparatus in accordance with claim 5, wherein said vibrator (33) comprises a compressed-air-operated needle (7) inserted into a root channel of a tooth (17) under examination.

7. An apparatus in accordance with claim 5 or 6, wherein said detecting apparatus (20) includes, an AM detector (28), for detecting the low-frequency vibrator signal in the echo pulse; a signal gate (26, 25) for gating out the detected vibrator signal,
    and a rectifier (31), for rectifying the filtered signal, whereby interface locations of the vibrating object, at least, at least, can be determined from the time relationship of the maximum value of the rectified signal to the ultrasonic pulse transmitted.

8. An apparatus in accordance with claim 7, wherein the filter (29) comprises a bandpass filter having a center frequency tuned to the frequency of said vibrator.

9. A method in accordance with claim 1 wherein said step of generating a high-frequency ultrasonic pulse comprises generating a pulse having a frequency in the range of 3...15MHz and said step of vibrating comprises vibrating the object under examination at a frequency in the range of 100...1000Hz.

10. An ultrasonic method for examining an ultrasonic medium including dense tissues, said method being repetitively performed at periodic intervals, comprising the steps of:
    generating a high-frequency ultrasonic pulse by means of an ultrasonic source (36),
    transmitting the ultrasonic pulse to an object (17) under examination,
    converting echo signals returning from the object (17) into electric signals,
    determining the intensity and delay of returning echo signals in relation to the pulse transmitted to the object under examination, generating an image of the measured object (17) under examination from the determined delay and intensity, vibrating the measured object (17) or the ultrasound source (36) at a low frequency, wherein the converting step further includes detecting and extracting a signal level of the low-frequency vibration signal from the echo signal in order to reveal the location of interfaces of the vibrating object (17) from the delays of the maximum values of the detected low-frequency signal relative to the transmitted high-frequency ultrasonic pulse; and wherein said object under examination comprises a tooth and said step of vibrating further includes inserting a vibrating needle into a root channel (30) of the tooth.

11. Ultrasonic measurement apparatus for examining an ultrasonic medium including dense tissues, comprising:

an ultrasonic pulse generator (24), for generating a drive signal, an ultrasonic transducer (36) connected to the pulse generator (24), said transducer converting the drive signal into an ultrasonic pulse transmitted towards an object (17) under examination, an ultrasonic receiver (36) for converting an ultrasonic echo pulse reflected from said object into an electric signal, and a measurement and analyzer system (19) coupled to the receiver (36) for determining the intensity and delay of a vibration signal received by the receiver (36) in relation to the ultrasonic pulse transmitted for generating a model of said object under examination, said system further comprising, a vibrator (33) for vibrating said object (17) or the ultrasound transmitter (36) with relatively low frequency signal, detection apparatus (20) coupled to said receiver (36), for detecting the level of the low-frequency vibrator signal from the echo signal for determining the interface locations of said object (17) from the maximum values of the low-frequency vibrator signal in relation to the drive signal, and wherein said vibrator (33) comprises a compressed-air-operated needle (70) inserted into a root channel of a tooth (17) under examination.

* * * * *